(12) United States Patent
Beck

(10) Patent No.: US 9,918,798 B2
(45) Date of Patent: Mar. 20, 2018

(54) ACCURATE THREE-DIMENSIONAL INSTRUMENT POSITIONING

(71) Applicant: Paul Beck, Atlanta, GA (US)

(72) Inventor: Paul Beck, Atlanta, GA (US)

( * ) Notice: Subject to any disclaimer, the term of this patent is extended or adjusted under 35 U.S.C. 154(b) by 427 days.

(21) Appl. No.: 14/730,909

(22) Filed: Jun. 4, 2015

(65) Prior Publication Data

US 2016/0354152 A1 Dec. 8, 2016

(51) Int. Cl.
| | |
|---|---|
| *A61B 19/00* | (2006.01) |
| *A61B 34/10* | (2016.01) |
| *A61B 34/20* | (2016.01) |
| *A61B 90/00* | (2016.01) |

(52) U.S. Cl.
CPC .............. *A61B 34/10* (2016.02); *A61B 34/20* (2016.02); *A61B 2034/107* (2016.02); *A61B 2034/2063* (2016.02); *A61B 2034/2065* (2016.02); *A61B 2090/364* (2016.02); *A61B 2090/373* (2016.02); *A61B 2090/378* (2016.02); *A61B 2090/3762* (2016.02)

(58) Field of Classification Search
CPC ...... A61B 2034/107; A61B 2034/2063; A61B 2034/2065; A61B 2090/364; A61B 2090/373; A61B 2090/3762; A61B 2090/378; A61B 34/10; A61B 34/20
See application file for complete search history.

(56) References Cited

U.S. PATENT DOCUMENTS

| | | | |
|---|---|---|---|
| 5,591,192 A | 1/1997 | Privitera et al. | |
| 7,491,198 B2 | 2/2009 | Kockro | |
| 7,751,865 B2 | 7/2010 | Jascob et al. | |
| 8,848,982 B2 | 9/2014 | Ren et al. | |
| 8,882,657 B2 | 11/2014 | Ohline et al. | |
| 2007/0204671 A1* | 9/2007 | Sliwa, Jr. | G01H 9/00 73/1.83 |
| 2011/0270084 A1 | 11/2011 | Choi et al. | |
| 2012/0046536 A1 | 2/2012 | Cheung et al. | |

(Continued)

FOREIGN PATENT DOCUMENTS

WO 2012/088535 6/2012

OTHER PUBLICATIONS

International Searching Authority, International Search Report and Written Opinion dated Aug. 5, 2016, issued in connection with International Patent Application No. PCT/US2016/031409, dated May 9, 2016, 12 pages.

(Continued)

*Primary Examiner* — Ruth S Smith
(74) *Attorney, Agent, or Firm* — McDonnell Boehnen Hulbert & Berghoff LLP

(57) ABSTRACT

A device may include a three-dimensional image sensor configured to scan an area including a closed or partially closed container, an output display, and a controller. The controller may be configured to: recognize an instrument that is detected by the three-dimensional image sensor, where a first section of the instrument is located inside of the container and a second section of the instrument is located outside of the container, and represent, on the output display, three-dimensional positions and orientations of the instrument, where a first position and a first orientation of the first section of the instrument is inferred from a second position and a second orientation of the second section of the instrument.

13 Claims, 13 Drawing Sheets

(56) References Cited

U.S. PATENT DOCUMENTS

2012/0323364 A1 12/2012 Birkenbach et al.
2013/0267833 A1 10/2013 Schroeder
2014/0135746 A1 5/2014 Schoepp
2014/0171962 A1 6/2014 Kang
2014/0378995 A1 12/2014 Kumar et al.

OTHER PUBLICATIONS

Kinect, Wikipedia, http://en.wikipedia.org/Kinect, Jun. 4, 2015, 20 pages.
Leap Motion, Wikipedia, http://en.wikipedia.org/Leap_Motion, Jun. 4, 2015, 5 pages.
PrimeSense, Wikipedia, http://en.wikipedia.org/PrimeSense, Jun. 4, 2015, 6 pages.

* cited by examiner

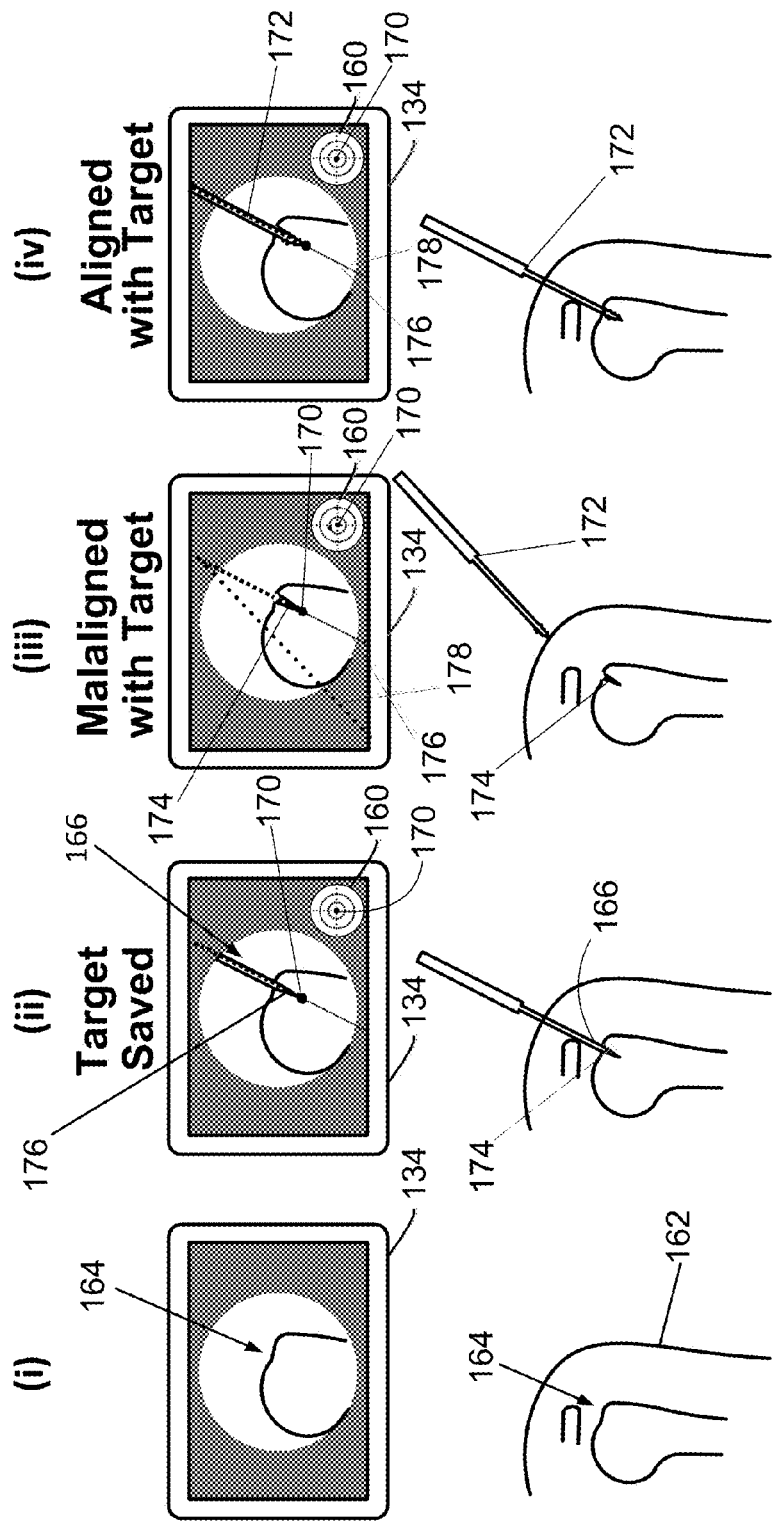

ACCURATE THREE-DIMENSIONAL INSTRUMENT POSITIONING

BACKGROUND

Precise positioning of instruments within a closed or semi-closed container is common in many industries. In the field of medicine, health care professionals routinely place instruments within a body (e.g., a human body) to aspirate fluid, obtain tissue biopsies, gain vascular access, place orthopedic hardware, and perform arthroscopies and/or laparoscopies.

These procedures are difficult because the health care professional cannot see the path the instrument tip will take once introduced into the body. As a result, the health care professional must use anatomic landmarks and other contextual cues outside the body to triangulate the precise position of instruments within the body to avoid critical structures and obtain the desired position. Unfortunately, this triangulation skill is difficult to obtain, often requiring repetition through trial and error. Even when this skill is acquired, the procedure can still be extremely difficult when an uncommon or new procedure is performed, when a patient has unusual anatomy, or when a patient is obese. In particular, anatomic landmarks of obese patients are hidden, and their anatomic structures are deeper within the body. Adding to this difficulty is that these procedures are often performed under strict time constraints, and failure can have serious consequences.

Complications during or after these procedures are not uncommon. These complications include, but are not limited to, infection as a result of an inefficiently performed procedure, failure to diagnose as a result of not obtaining diseased tissue during a biopsy, excess bleeding as a result of repeated instrument passes or instrument passes through critical structures, spreading of a tumor as a result of multiple passes through a tissue site, and ill-placed hardware resulting in an unsuccessful procedure.

SUMMARY

A first example embodiment may involve (i) a three-dimensional image sensor configured to scan an area including a closed or partially closed container, (ii) an output display, and (iii) a controller. The controller may be configured to recognize an instrument that is detected by the three-dimensional image sensor, where a first section of the instrument is located inside of the container and a second section of the instrument is located outside of the container, and represent, on the output display, three-dimensional positions and orientations of the instrument, where a first position and a first orientation of the first section of the instrument is inferred from a second position and a second orientation of the second section of the instrument.

A second example embodiment may involve recognizing, by a three-dimensional image sensor, an instrument. A first section of the instrument may be located inside of a closed or partially closed container and a second section of the instrument may be located outside of the container. The second example embodiment may also involve representing, on an output display communicatively coupled to the three-dimensional image sensor, three-dimensional positions and orientations of the instrument. A first position and a first orientation of the first section of the instrument may be inferred from a second position and a second orientation of the second section of the instrument.

In a third example embodiment, an article of manufacture may include a non-transitory computer-readable medium, having stored thereon program instructions that, upon execution by a computing device, cause the computing device to perform operations in accordance with the second example embodiment.

In a fourth example embodiment, a computing device may include at least one processor, as well as data storage and program instructions. The program instructions may be stored in the data storage, and upon execution by the computing device may cause the computing device to perform operations in accordance with the second example embodiment.

A fifth example embodiment may involve (i) a system including a three-dimensional image sensor configured to scan a closed or partially closed container, (ii) an output display, and (iii) a computing device communicatively coupled to the three-dimensional image sensor and the output display. The computing device may include a processor and data storage, and instructions stored in the data storage may be executable by the processor to perform operations including: recognizing an instrument that is detected by the three-dimensional image sensor, where a first section of the instrument is located inside of the container and a second section of the instrument is located outside of the container, and representing, on the output display, three-dimensional positions and orientations of the instrument, where a first position and a first orientation of the first section of the instrument is inferred from a second position and a second orientation of the second section of the instrument.

In a sixth example embodiment, a system may include various means for carrying out each of the operations of any of the previous example embodiments.

These as well as other embodiments, aspects, advantages, and alternatives will become apparent to those of ordinary skill in the art by reading the following detailed description, with reference where appropriate to the accompanying drawings. Further, it should be understood that this summary and other descriptions and figures provided herein are intended to illustrate embodiments by way of example only and, as such, that numerous variations are possible. For instance, structural elements and process steps can be rearranged, combined, distributed, eliminated, or otherwise changed, while remaining within the scope of the embodiments as claimed.

BRIEF DESCRIPTION OF THE DRAWINGS

FIG. 10A depicts saving the position of an instrument during a procedure, then using the saved position to determine the alignment of another instrument used during the procedure, in accordance with example embodiments.

DETAILED DESCRIPTION

Figure 1:
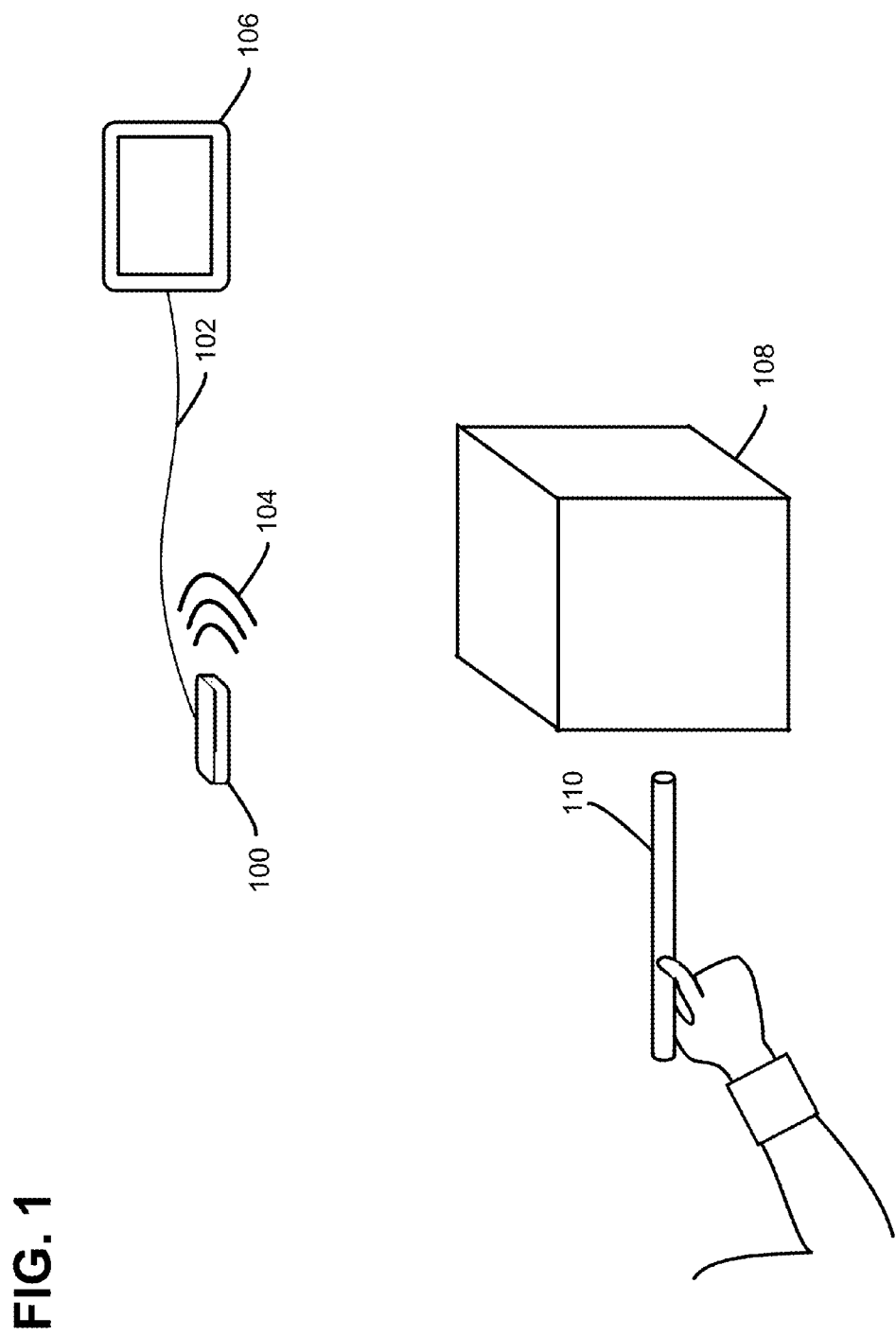
FIG. 1 is a frontal view showing a sensor device positioned above a closed container, an instrument positioned outside the closed container, and a computer display connected to the sensor device.

Example methods, devices, and systems are described herein. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Other embodiments can be utilized, and other changes can be made, without departing from the scope of the subject matter presented herein.

Thus, the example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

Further, unless context suggests otherwise, the features illustrated in each of the figures may be used in combination with one another. Thus, the figures should be generally viewed as component aspects of one or more overall embodiments, with the understanding that not all illustrated features are necessary for each embodiment.

1. OVERVIEW

In order to overcome problems associated with instrument placement, many different instruments and imaging techniques have been developed. Each technique has its own unique advantages, but each also has significant limitations. For example, in tissue biopsies and vascular access procedures, a user attempts to place a needle within a tissue to obtain a sample of that tissue, or within a blood vessel to pass a monitoring device or obtain blood (herein, the term "user" may refer to a health care professional, such as a doctor, nurse, medical assistant, and so on, though the term is not limited to these types of users). With each procedure, an ultrasound device can be used to help the user visualize some of the structures beneath the skin of the patient. However, the procedure is still quite challenging as the ultrasound transducer (the part of the ultrasound device that is typically placed against the patient's skin and converts received ultrasound signals to electrical signals for display on an associated monitor) cannot see or represent the needle's position or direction outside of the patient's skin. As a result, the user attempts to triangulate to a point deep within the body by trying to align the ultrasound transducer and the needle tip, in the hope that the needle's path is in line along all planes with the desired point, and not in line with a critical structure that should be avoided. Additional complexity is added, as the angle at which ultrasound waves encounter the surface of a structure (referred to as the angle of incidence) affects the way the structure is presented on the screen of the ultrasound device. If the angle of the needle becomes more parallel to the surface of the object, the image of the needle has less definition and might not be clearly visualized.

To make triangulation easier, alignment guides may be attached to an ultrasound transducer. An alignment guide is used to fix the plane of the needle in line with the plane of the ultrasound transducer. However, this device still has significant limitations. Alignment guides still require that the user estimate the plane in which the needle needs to be directed when entering the skin to obtain the desired depth on the ultrasound display. This is because ultrasound-based alignment can only align a needle in a single plane (e.g., in just one of an X/Y, X/Z, or Y/Z plane). Thus, information about the alignment of the needle in the third dimension is missing. As a result, the user must still use vague contextual cues and personal experience to direct the needle while avoiding vital structures.

Unfortunately, alignment guides are also limited to one plane of alignment relative to the ultrasound transducer, typically in-plane. As a result, when using an alignment guide, the user cannot position the needle out of this plane, which may be required to avoid vital structures within the body.

As alignment guides have significant limitations, an improved ultrasound device can use an ultrasound transducer, optics, magnetic needles, and an alignment guide to track a needle for vascular access procedures. However, the ultrasound transducer must be modified to provide the alignment guide and optical recognition. As a result, using this technique involves using specialized attachments that are connected to the transducer. Furthermore, this technique also uses a specialized magnetic needle. Since this device cannot be used with most existing ultrasound transducers and does not use standardized needles, it is extremely limited in terms of cost and access. Additionally, since the device uses a non-standard ultrasound transducer, non-standard transducer attachments, and non-standard magnetic needles, the health care provider loses the "feel" of being able to place instruments precisely, and must relearn a procedure for which they have already become comfortable. Finally, like the alignment guides, this device is limited as it cannot be aligned out-of-plane of the ultrasound. As a result, its ability to avoid structures within the body is significantly limited.

Computed tomography (CT) guided tissue biopsies may be used to position needles in multiple planes. Unfortunately, this procedure typically is conducted in a radiology center or an imaging department within a hospital. To perform the procedure, a trained radiology technologist operates the CT scan, while the user performs the procedure. As a result, this method has several limitations. The patient and user are exposed to repeated or continuous radiation that can be harmful to human tissue. In addition, the procedure cannot be performed at the bedside or within an operating room, thus limiting its access. Finally, the procedure is expensive as it requires a radiology technologist and the overhead costs associated with the CT scanner and imaging center.

The skills required to triangulate instruments in three dimensions are used in most fields of medicine. In orthopedic surgery, for example, a health care team may be reliant on their ability to triangulate multiple instruments both in and out of the human body. Examples procedures in which this ability may be used include joint arthroscopy, trauma, and spine stabilization.

In joint arthroscopy, a surgeon places an instrument that contains a camera within a joint. Then, the surgeon may place a second instrument within the joint, the second instrument out-of-plane with the camera. But when it is positioned correctly, the second instrument is within the visual field of the camera. To do this, the surgeon will estimate both the entrance point on the skin and the direction that the instrument is to enter. As a result, when the instrument is placed in the joint, it is visualized by the camera deep within the joint while avoiding vital structures within the body. For example, triangulation may be used hundreds of times during routine shoulder arthroscopy and from many different entry points. This makes the ability to triangulate accurately and efficiently highly desirable in order to obtain a successful procedural outcome, avoid complications, and reduce operating room costs.

Prior to the present embodiments, a device for arthroscopic procedures that enables the surgeon to track the location of instruments in real time or near real time during the triangulation of the instruments did not exist. Alignment guides for drills do exist, but they are limited to drill guides and can only be used after the surgeon has already triangulated its position into the joint. As a result, arthroscopy can be extremely challenging for patients with abnormal anatomic landmarks, for procedures such as hip arthroscopy that are deep below the skin and surrounded by critical structures, and for obese patients that have hidden anatomical landmarks.

Even in patients with relatively normal anatomy, these procedures are especially challenging for a surgical assistant. The assistant may be working from a different vantage point from the surgeon and may lack the contextual cues that the surgeon is using during the procedure. A phrase commonly used to describe this frustration by the assistant who is having difficulty is "everything is backwards."

In trauma and spine fixation procedures, an instrument is commonly aimed within a bone in order to cross a fracture site or to stabilize the bone. To assist the surgeon, C-arm fluoroscopy or an X-ray imaging device may be used so that the path of the instrument through the bone can be visualized. Unfortunately, these imaging modalities are limited as they can only obtain information about the direction and position of an instrument in a single plane at any one time. As a result, using imaging to place and direct an instrument is imperfect as the surgeon is attempting to direct the instrument simultaneously across multiple planes in order to obtain the correct starting point, path, and final positioning of the instrument. To account for this limitation, the imaging device is often moved into another plane to help the surgeon direct the instrument across the multiple planes. As a consequence, the surgeon cannot track the instrument in real time or near real time in both planes. The result is that the surgeon often uses contextual cues for planes not visualized on the imaging device.

Triangulation of instruments during a trauma procedure involves careful positioning of the patient, a well-trained and experienced radiology technologist, and a skilled surgeon to be successful. Regrettably, as trauma is often performed at night, these procedures may not performed by the most skilled, experienced, or well-rested personnel. Moreover, the anatomy of the patient's body is often distorted by trauma and obesity, which can make these procedures exceedingly difficult. As a result, the patient and operating room team is often exposed to significant radiation, and complications are common if the procedure is protracted and/or performed poorly.

Recently, surgical navigation has been introduced to enable a surgeon to track the both the position and direction of surgical instruments simultaneously along multiple planes within the surgical field. While this method has the potential to improve triangulation by enabling the surgeon to track instruments in real time or near real time within multiple planes, it is still significantly limited. Current surgical navigation requires a large, protuberant attachment to each instrument that is triangulated within the operative field. As a result, instruments must be modified to include the specialized attachment, and therefore hospitals and clinics have to purchase these expensive new instruments. Additionally, as the attachment is large and extends from the instrument, it can have the following drawbacks: (1) it can adversely affect the balance and feel of traditional instruments, resulting in the loss of the feel that the surgeon uses to finely place instruments, (2) it adversely affects positioning of the instrument as the surgeon not only pays attention to the instrument direction, but also the direction of the attachment so that it is visible to the surgical navigation device, (3) it may hinder the correct positioning of the instrument in tight spaces to the extent that the surgeon may not be able to use the device, and (4) it cannot be used across multiple fields of medicine because not all devices have been modified to utilize surgical navigation.

In summary, existing alignment techniques and devices are limited, expensive, and specialized. They do not work across multiple disciplinary fields and many cannot be used to perform different procedures within a field. In addition, they use unfamiliar, often bulky instruments that result in the loss of the feel a health care professional uses to precisely position instruments. None of the above described devices enable the health care professional to triangulate the position of an instrument using existing devices, ones that are familiar and readily accessible. Further, the positioning devices are not readily usable across all fields including all medical fields. It is this problem that the embodiments described below address and, as a result, make these procedures safer, more available, and at far lower costs. Nonetheless, the embodiments herein may have other uses outside of those disclosed in this specification, including outside of the field of medicine.

The embodiments herein are generally directed to improving the ability of a user to triangulate an instrument within a closed or semi-closed body. These embodiments enable a user to precisely place an instrument or instruments within a closed or semi-closed container without direct visualization of the instrument tip within the closed or semi-closed container. While these embodiments may include a device to be used with alignment guides, it is not limited by the plane of alignment guides and is able to localize anywhere within a three-dimensional environment. While this device may track instruments of known size and/or length, it is not limited to such instruments. For instance, the device may be used to determine the size, including the length, of instruments within its visual field. The device enables a user to track the position of an instrument or instruments outside and inside the closed or semi-closed container in real time or near real time.

The embodiments herein may be used across multiple fields. In medicine, this includes, but is not limited to, biopsies, vascular access procedures, arthroscopy and/or laparoscopy, orthopedic trauma, and orthopedic hardware placement. As a result of its use across multiple fields, a device incorporating the embodiments can be inexpensive and familiar to the user. While this device may be used with specialized attachments to establish the orientation and motion of an instrument, it is not required to use the attachments. As a result, the device is unique as it can be used with existing, non-modified instruments. The ability to use existing instruments may reduce costs associated with these procedures while maintaining the feel and familiarity to precisely perform delicate procedures, thereby reducing the risk of these procedures.

While other devices may be used as adjuncts, such as optical devices or imaging (e.g., X-ray, CT, ultrasound, etc.), they are not required. Additionally, the device will not expose the patient or healthcare team to dangerous radiation and will not need to be used in specialized facilities.

The device may include a single sensor or multiple sensors. It may be flexible, and can be used for nearly any procedure that requires precise triangulation of one or more instruments. The device may be available at decreased costs, as it does not required specialized personnel to operate and can be used in conjunction with standard computer systems. While the use of proprietary devices is possible, the device may enable the user to use existing imaging and instrument targeting systems. While the device can be used for medical procedures, both human and animal, it is not limited to these modalities and can be used for any application that requires precision targeting and manipulation of instruments.

In particular, a sensor or sensors may be placed within a working field. The sensor may consist of one or more cameras and one or more light-emitting diodes. However, other sources of electromagnetic energy may be used. Image capture may be done using any conventional technology capable of capturing instruments and motion in three-dimensional space.

The sensor may track the size, position, direction and/or motion of one or more reference objects in three dimensions. The sensor may register each end of the instrument and any attachments or extensions of the instrument. Software contained within the sensor and/or on a computing device attached to the sensor may display a digital representation of the detected object(s). The digital representation may be viewed on a viewing display such as a monitor or screen. Different display types include, but are not limited to, traditional mobile computers such as cell phones and tablet computers, desktop clients, television, and head-mounted displays. Alternatively or additionally, the viewing display may be contained within the sensing unit (e.g., in an integrated tablet) or within a virtual reality system.

Software may be used to distinguish human body parts, joints and movements. This may include any person within the field of the sensor. However, the sensor might not be limited to detecting instruments and human body parts. The sensor may detect and display any object within its visual field.

In an example embodiment, a sensor is placed such that its field of sensing encompasses the physical area in which a medical procedure is taking place. The sensor may be directed to capture the size, position, and movements of instruments used during the medical procedure. The sensor is attached to a computing device either by a direct connection (e.g., wired universal serial bus (USB)), wirelessly (e.g., Wifi or Bluetooth) or may be an all-in-one computing device. The sensor, computing device, and/or display may contain software that may display a representation of objects within the sensor field, including instruments.

A user may register an instrument by placing the instrument within the field of the sensor. Software used by the sensor may determine the instrument's physical parameters including its length, width, position, and direction. These measurements of an instrument's dimensions may be accurate to within one millimeter or less.

Any extensions or attachments may also be registered by the software. Registration may be automatic or activated by voice command, foot or hand pedals, motion of the user, or by direct input on the computing device. The registration may be confirmed by the user. The software may store a representation (e.g., a computer-aided design (CAD) file) of the registered instrument within a database so that the instrument may be automatically identified throughout the procedure or during subsequent procedures. Alternatively, the physical parameters of instruments for a particular procedure may be stored within a database prior to a procedure. The software may then automatically identify each instrument as it is brought into the sensing field by referencing the database. The user may have the option to confirm the instrument as identified. However, registration is not required. Any instrument brought within the visual field of the sensor may have any of its attributes measured automatically including its size, position, direction, and motion.

Once an instrument has been detected, it may be tracked by the sensors. However, the device does not require visualization of the entire instrument. Since the device may know the size of an object, including it length, part of the object may be placed outside the visual field of the device and still be tracked. For example, if a portion of an instrument were placed in a closed container (e.g., a patient's body), the device would be able to extrapolate the precise position of the instrument within the container, as the device knows the position and direction of the remaining portion of the instrument outside the closed container. The device may display the instrument, including both the visualized and non-visualized portion.

As a result, although the user might not be able to see the three-dimensional position of the entire instrument within the closed container, the user may know the precise position and orientation of the instrument in three dimensions by viewing the display. However, if the sensor cannot determine the exact location of the device within the container, for example a hand or other device impedes visualization of part of the device, longitudinal information may still be provided to the user that enables the user to triangulate.

A second instrument may be brought into the visual field of the device. As mentioned above, the second instrument may be registered prior to or during the procedure and then virtually displayed. As the localization device may track and display the three-dimensional locations and trajectories of both instruments in real time, the user may triangulate both instruments on the virtualized display. For example, the user may place an end of the second instrument against the outside of the closed container. The user may then direct the second instrument such that it is pointed in the direction of the tip of the first instrument which was already placed within the closed container. Using real time tracking, the three-dimensional virtualized projection paths of both the first and second instrument can be viewed on a display. As a result, a precise entry point (e.g., skin location) for the second instrument that may avoid critical structures (e.g., vascular structures) deep within the closed container (e.g., a human body) may be determined. Once the entry point is chosen, the direction of the instrument may be precisely ascertained using the virtual display so that the instrument may be advanced to a specifically defined point relative to the first instrument (e.g., the tip of the first instrument). Advantageously, although only a portion of an instrument or instruments may be visualized by the human eye when partially placed within a closed container, the instruments may still be precisely positioned within the closed container by using the virtual display of the device.

Once an instrument is properly positioned in three dimensions, the user may save this three-dimensional position by voice command, foot or hand pedals, motion of the user, or by input on the computing device. As a result, when the instrument is removed, the desired position remains visualized on the virtual display creating a virtual target. This is especially desirable as it enables the user to position the same instrument or a second instrument through the same tissue path and in the same position as the original instrument.

The ability to save the instrument position(s) on the virtual display may have several advantages. It may help avoid injury to peripheral structures (e.g., muscle, artery, nerve etc.) as it enables the user to position a second instrument in the same plane as the first. It also may decrease soft tissue trauma and may decrease the potential spread of cancerous tissue by avoiding the passage of instruments through multiple tissue planes. It may decrease procedural time, and may reduce hardware malposition and/or failure. As a result, costs related to procedural time and complications may be dramatically reduced while reducing patient morbidity and mortality.

For example, a user may place an awl into the greater tuberosity of a shoulder during a rotator cuff repair. The final position of the awl may be saved on a virtual display, creating a virtual target for any subsequent instruments. Once this final position is saved, the user may remove the awl. A rotator cuff anchor inserter may then be positioned in the body through the same tissue plane by referencing the virtually saved position of the awl. In this example, the saved virtual position of the awl prevents the user from losing visualization of the original drill hole (a common problem), prevents multiple failed passes of the anchor inserter, and enables the user to place the anchor at the optimal angle and depth for fixation to bone.

The display of the sensing device may augment that of one or more other devices (e.g., x-ray or ultrasound devices) by integrating into the displays of these devices. In an example embodiment, the display of the sensing device may be placed over the image output of a second device display such that the position of the instruments in the display of the sensing device match the position of the instruments in the second device display. Alternatively, a representation of the display of the sensing device may be placed anywhere in the second device display so that the display of the sensing device may be referenced during a procedure.

Working as an adjunct to the second device display, the display of the sensing device may augment the second device display and enable a user to complete a procedure (e.g., c-arm, ultrasound, x-ray, arthroscopy etc.) more efficiently than using either alone. For example, a user may first register an arthroscopic camera prior to placing it inside a shoulder joint. The camera may then be placed within the joint. The sensor device may track in real time or near real time the position, direction and motion of the arthroscope. The sensor device may then register a second instrument, such as a needle, and track it in real time or near real time as well. The needle may then be placed against the skin of the patient and the virtualized projected path of the needle may be displayed over the arthroscopic display. Using direct arthroscopic visualization and the sensor device, the user may use the virtualized projected path to advance the needle to the tip of the arthroscope, or within the desired visual field of the arthroscope, using the device display and/or the augmented arthroscopic display.

While not required, tracking may be improved by using photographic edge detection. Edge detection may involve using one or more computational (i.e., mathematical) techniques to identify points of a digital image at which the brightness or color changes sharply or has discontinuities. These points may be organized into a set of straight or curved line segments referred to as edges. Thus, in addition to registering the physical shape of an instrument, the sensor device may identify additional physical parameters including markings (e.g., an etched laser line) using edge detection. The sensor may then track an instrument by both the physical parameters (e.g., shape etc.) of the device and/or image edge detection using existing markings on the instrument.

An advantage of edge detection is that the depth of an instrument may still be tracked even if certain physical landmarks are obscured that may be used for tracking. For example, a surgeon may triangulate a position to start an arthroscopic portal using a spinal needle. However, if the surgeon's hand is covering the end of a spinal needle, the sensing device may not be able to adequately track the depth of the needle since physical landmarks may be obscured. As a result, while useful information may still be available such as the direction of the needle, the depth of the tip of the needle might not be determined simply by using the shape of the needle. However, if the sensor device uses both the shape of the needle to determine its direction and edge detection of any additional markers on the needle, the sensor device may still accurately determine the depth of the needle when its end is covered by the surgeon's hand.

The sensor device can exist separate from other devices or may be embedded within another device(s) such as a computer, overhead lights, surgeon/assistant headpiece, or surgical light handles, etc. The software can be run locally or on any computing device, including from a web server.

While example displays are included herein, this is not to limit the types of information that are provided to the user of the sensing device. Any display method may be used that enables the user to determine the position of one instrument relative to the position of another instrument. Furthermore, the device is not limited to a visual display. Other methods that may be employed include audible and tactile instruction(s) to the user. For example, in addition to the visual cues on the display(s), a user may be instructed using an audible signal to either lift or lower the hand thereby allowing the using to efficiently triangulate to a position.

As such, these embodiments are not limited to a specific field. In addition to the uses described above, the present embodiments can be used by any field that requires the precise tracking and manipulation of one or more objects in two or three dimensional space. Moreover, the methods and devices disclosed herein may operate on or make use of a wide range of physical or logical visual display and computer hardware components, and may be implemented on any type of software platform.

2. EXAMPLE DEVICE AND OPERATION

Referring now to FIG. 1, a method and system is depicted for positioning an instrument within a closed container. A workspace may include a sensor 100 or sensors placed above a closed or semi-closed container 108, and an instrument 110. Sensor 100 may be connected to a primary sensor computer display 106 either by a wired connection 102 or a wireless connection 104. Sensor 100 may include one or more cameras and one or more light-emitting diodes. Sensor 100 and display 106 may communicate with a computer executing a stored program as will be described.

A depth sensing camera device believed to be suitable for the present embodiments is available commercially from Leap Motion of San Francisco, Calif., USA, for example the Leap Motion Controller. While it is one device that can track with millimeter-level resolution, other devices, including those created by Primesense of Tel Aviv, Israel, as well as the Kinect motion sensing input device by Microsoft, Inc. of Redmond, Wash., USA, may be able to perform this function at some point. However, tracking can be done using any conventional technology capable of capturing positions, gestures, and motion in three-dimensional space.

By using a light emitter such as a light emitting diode or an infrared source of light, as well as an optical sensor such as one or more cameras, an instrument or instruments can be precisely located and tracked. Particularly, the device may use the light and the optical sensor to determine the precise location of objects in three-dimensional space. For instance, the device analyzes objects observed in the device's field of view, recognizing discrete positions, gestures and motions.

The device may also be able to determine the shape and length of an instrument such that it may: 1) Calculate the central axis of the instrument and create a virtual pointer on a display that extends beyond the length of its axis for targeting; 2) calculate the length of an instrument so that when the instrument is placed within a closed or partially-closed structure (for example a body of a human or another organism), the position within the body that is not visualized by the user or the device may be determined; 3) calculate the position of a random point or structure on the instrument so that it may use that point as a reference to determine the position of the instrument tip within the structure; and 4) use a point on the instrument to determine the direction a camera is viewing such as when performing arthroscopy. In an alternative embodiment, the device may track just direction, without recording instrument length or position.

For example, the device may emit a light pattern onto objects in the sensor field. This light pattern may be formed with light that is not in the visible spectrum, so that it is not distracting to users. The light pattern may define a physical grid so that other cameras or sensors on the device may sense objects within the field. To that end, one or more cameras that may be synchronized to the emission of the light pattern may capture the grid as it is laid out. The camera may feed the captured grid into an algorithm that produces a three-dimensional representation of the scene on the device.

In some embodiments, more than one three-dimensional sensor may be used to improve spatial tracking. For example, multiple three-dimensional sensors may be used to obtain additional information about the field of interest or to enlarge the field of interest. In another embodiment, edge detection algorithms may be used to improve tracking of the device. Thus, the device might not be limited by spatial tracking Edge detection may also be used during processing of data to assist the user during display output.

Figure 2:
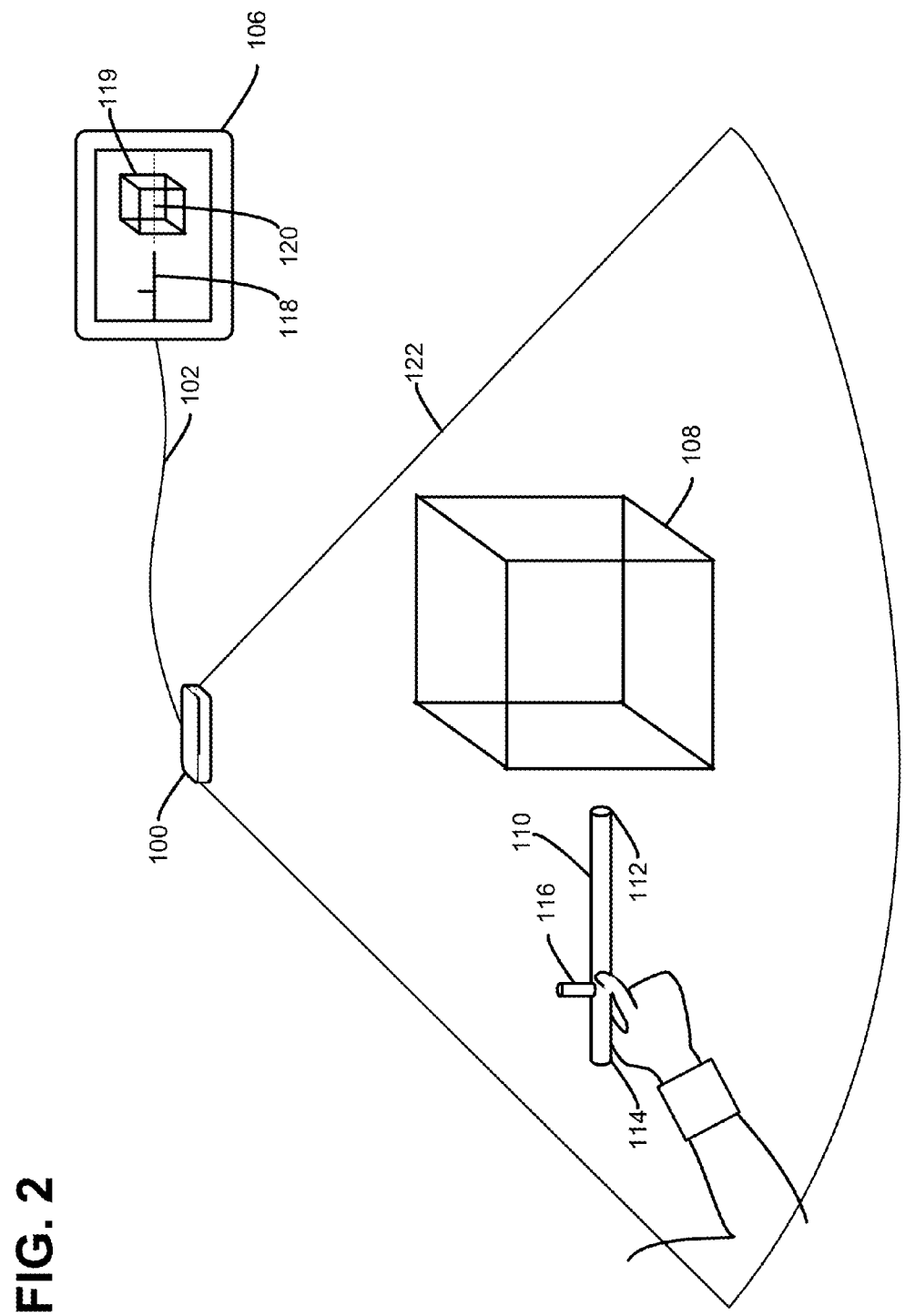
FIG. 2 is a frontal view illustrating an instrument outside a closed container being registered by the sensor and being virtually displayed on a computer display, in accordance with example embodiments.

Referring now to FIG. 2, sensor 100 may register a position of instrument 110. The longitudinal axis of instrument 110 may be calculated (in some cases, an axis other than or as well as the longitudinal axis may be determined). Additionally, the length of instrument 110 may be entered into a computer associated with display 106, or alternatively may be measured by sensor 100 from the front end 112 of instrument 110 to the back end 114 of instrument 110. The position of any secondary instrument projection 116 (e.g., an arm) of instrument 110 may be entered in the computer associated with display 106 or measured by sensor 100 to assist in the tracking of instrument 110.

Display 106 displays virtual position 118 of instrument 110 and the virtual position 119 of container 108. As the longitudinal axis of instrument 110 may have been registered, the projected instrument path 120 (e.g., its longitudinal axis) may also be displayed.

Figure 3:
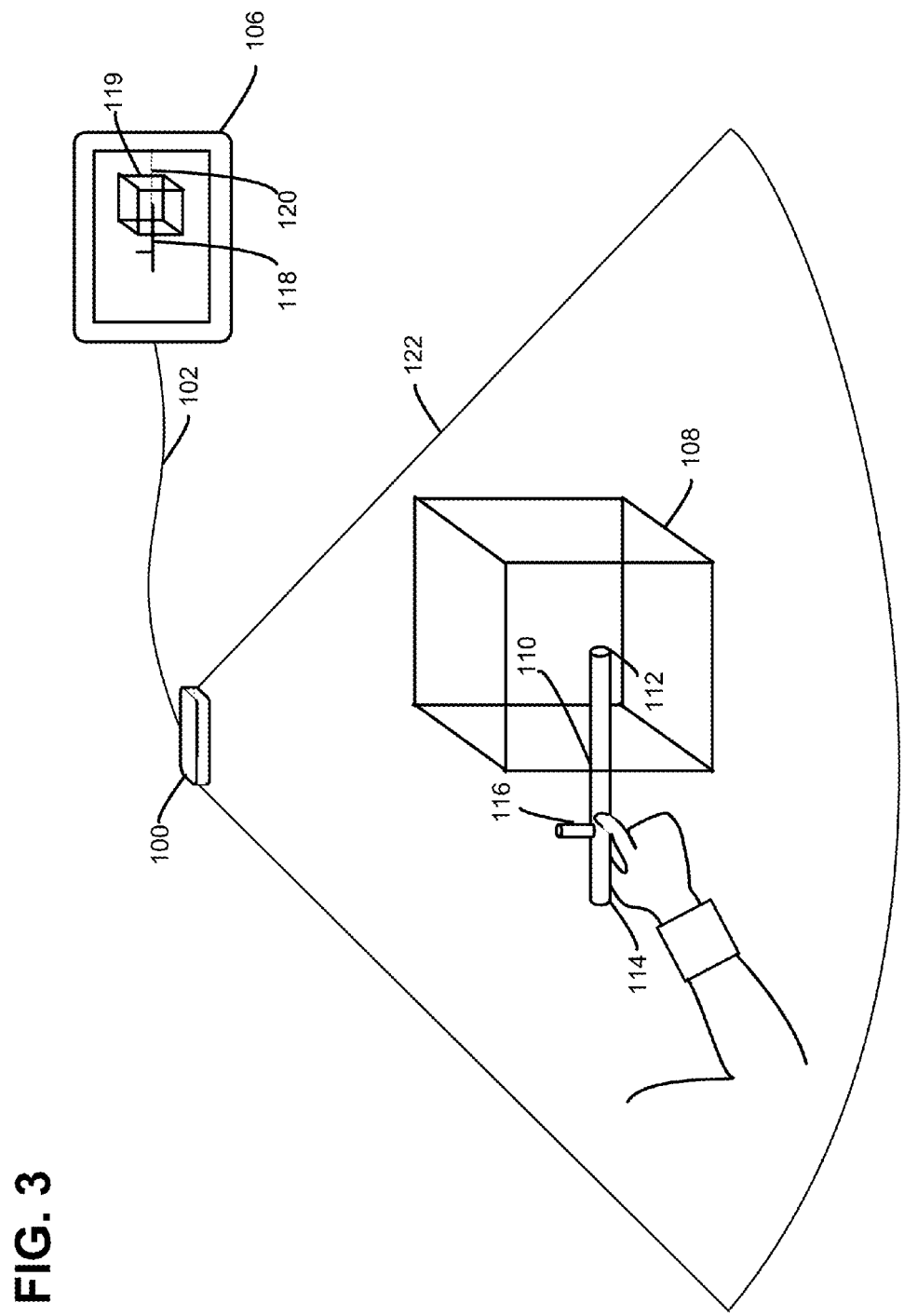
FIG. 3 is a view depicting the tracking of the instrument as its leading tip is positioned within a closed container and the associated display of the instrument on a computer, in accordance with example embodiments.

Referring now to FIG. 3, the front end 112 of instrument 110 is moved within container 108. Although the part of instrument 110 placed within the contained may no longer be visible to the sensor, the position of the part of instrument 110 placed within container 108 may be represented on display 106 because the length of instrument 110 from front end 112 to back end 114, or from front end 112 end to secondary instrument projection 116 was entered or measured, and the longitudinal axis was registered prior to instrument 110 being placed in container 108. Using the registered data prior to placing part of instrument 110 within container 108 and the sensor data obtained by the still visible portion of instrument 110, the computer may calculate and display a virtual representation 118 of the entirety of instrument 110, as well as its longitudinal axis 120, on display 106.

Figure 4:
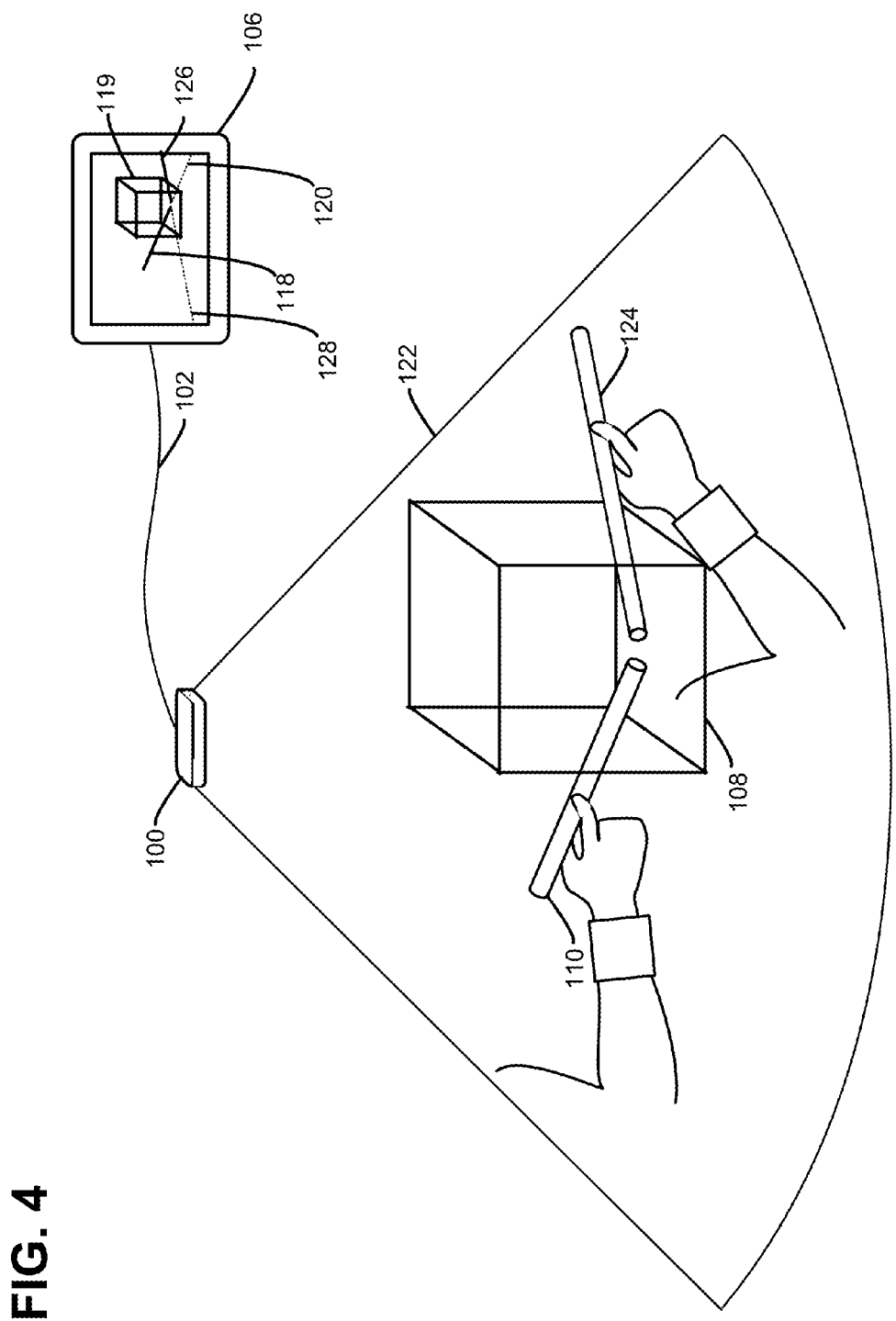
FIG. 4 depicts a computer display of two instruments that are being tracked and as they are manipulated within a container, in accordance with example embodiments.

Referring now to FIG. 4, after being registered, instrument 110 is placed within container 108, and a second instrument 124 is then registered and placed within container 108. The two instruments may be placed within container 108 and their respective positions may be triangulated relative to each other. The system may be able to track more than just two instruments. Display 106 may display a virtual representation 118 of instrument 110 and its projected instrument path 120, as well as a virtual representation 126 of instrument 124 and its projected instrument path 128.

Figure 5:
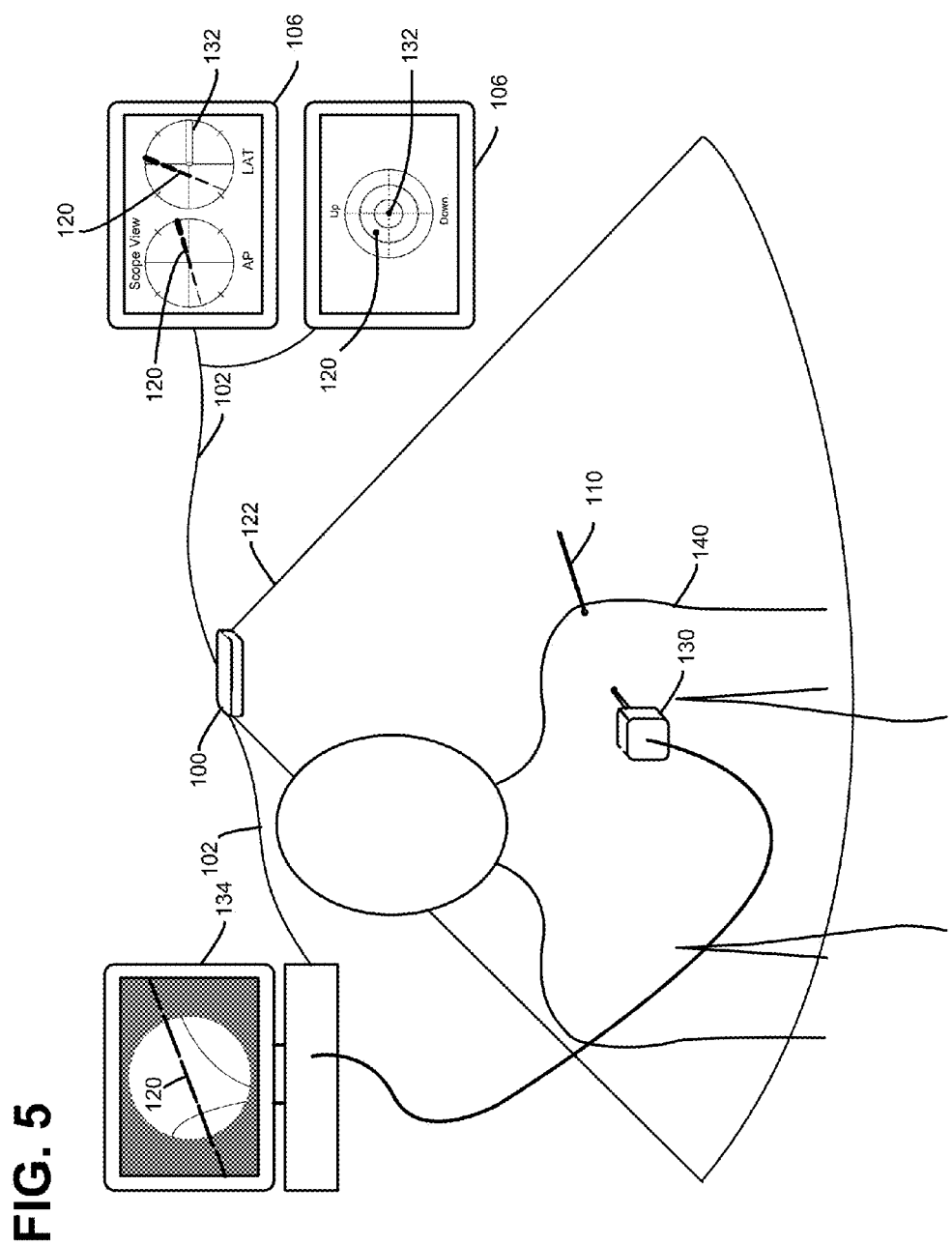
FIG. 5 illustrates a use case in arthroscopic surgery where an instrument is being triangulated into a joint relative to an arthroscope and/or being displayed on a computer as an augmented overlay over the arthroscopic camera view and a primary display, in accordance with example embodiments.

Referring now to FIG. 5, sensor 100 is placed over the shoulder of a patient's body 140. The placement of sensor 100 is so that the sensor field can register the patient's body 140 and instruments placed in and out of the patient's body 140. In FIG. 5, an arthroscopic camera 130 is registered by sensor 100 and then placed in the shoulder joint of a patient's body 140. A instrument 110 is registered and placed within the shoulder joint of a patient's body 140. Sensor 100 sends its data to the computer associated with display 106. Display 106 shows a virtual view of instrument 110 relative to the arthroscopic camera 130. Projected instrument path 120 is shown in two orthogonal plane views on a virtual arthroscope 132 of display 106. However, display 106 is not limited to orthogonal views and may additionally display a three-dimensional rendered view.

In these types of procedures, the typical arthroscopic camera displays live video from within the shoulder joint. The data from sensor 100 may be displayed as an overlay over the arthroscopic video to create an augmented arthroscopic display 134. Augmented arthroscopic display 134 shows projected instrument path 120 of instrument 110 being placed within the shoulder joint of the body 140. Augmenting the view may enable the user to view the live video and triangulate to the arthroscopic camera 130 with instrument 110. The system may include either augmented arthroscopic display 134, display 106, or both.

Figure 6:
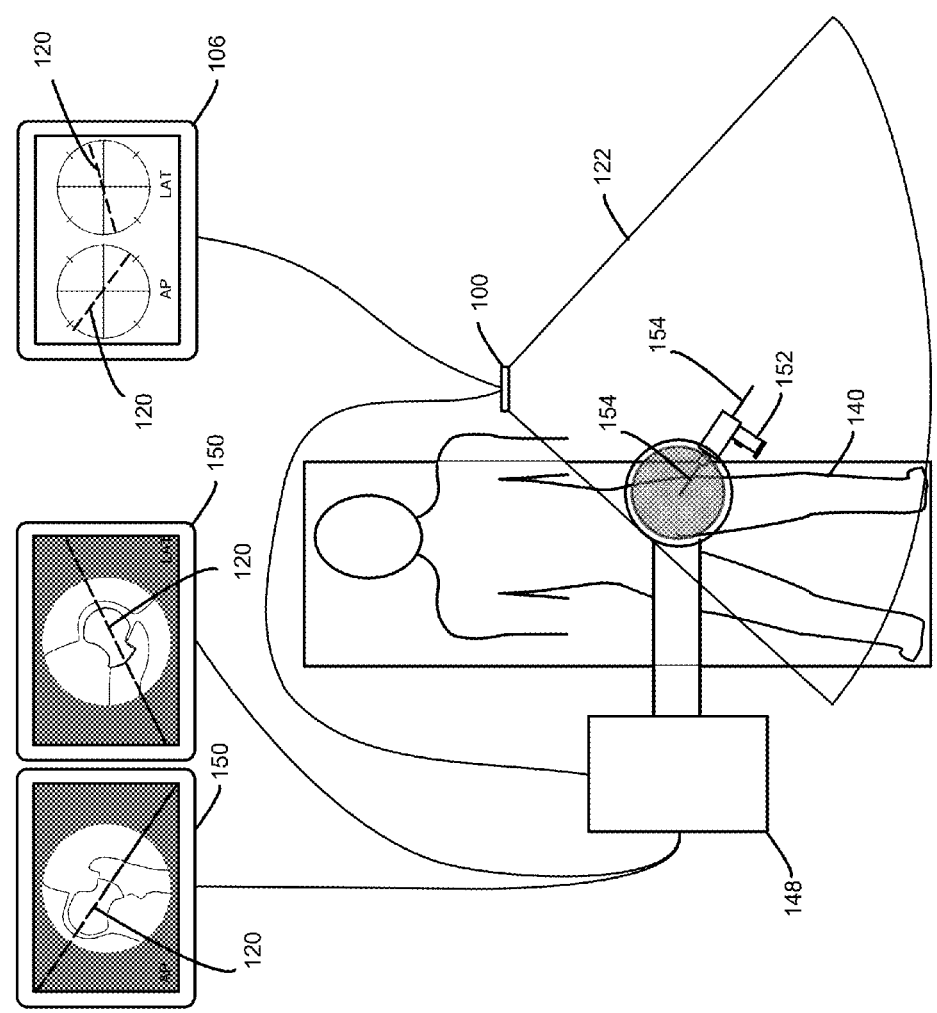
FIG. 6 illustrates a use case in orthopedic trauma surgery where the projection of an instrument across a fracture is used to position a drill wire on both an augmented and a primary display, in accordance with example embodiments.

Referring now to FIG. 6, in this embodiment, a patient's body 140 is shown with C-arm fluoroscopy (a mobile x-ray) 148 taking images of a fractured left hip and displaying them on augmented x-ray display 150. Sensor 100 is placed next to the patient's body 140 so that its sensor field 122 receives data from the patient's body 140, a drill 152, and a guide wire 154. Sensor 100 is connected to display 106 and the augmented x-ray display 150. Drill 152 is being used to direct guide wire 154 across the hip fracture, and the projected instrument path 120 of guide wire 154 is being displayed on augmented x-ray display 150. Display 106 also shows the projected instrument path 120 of the guide wire 154.

Figure 7:
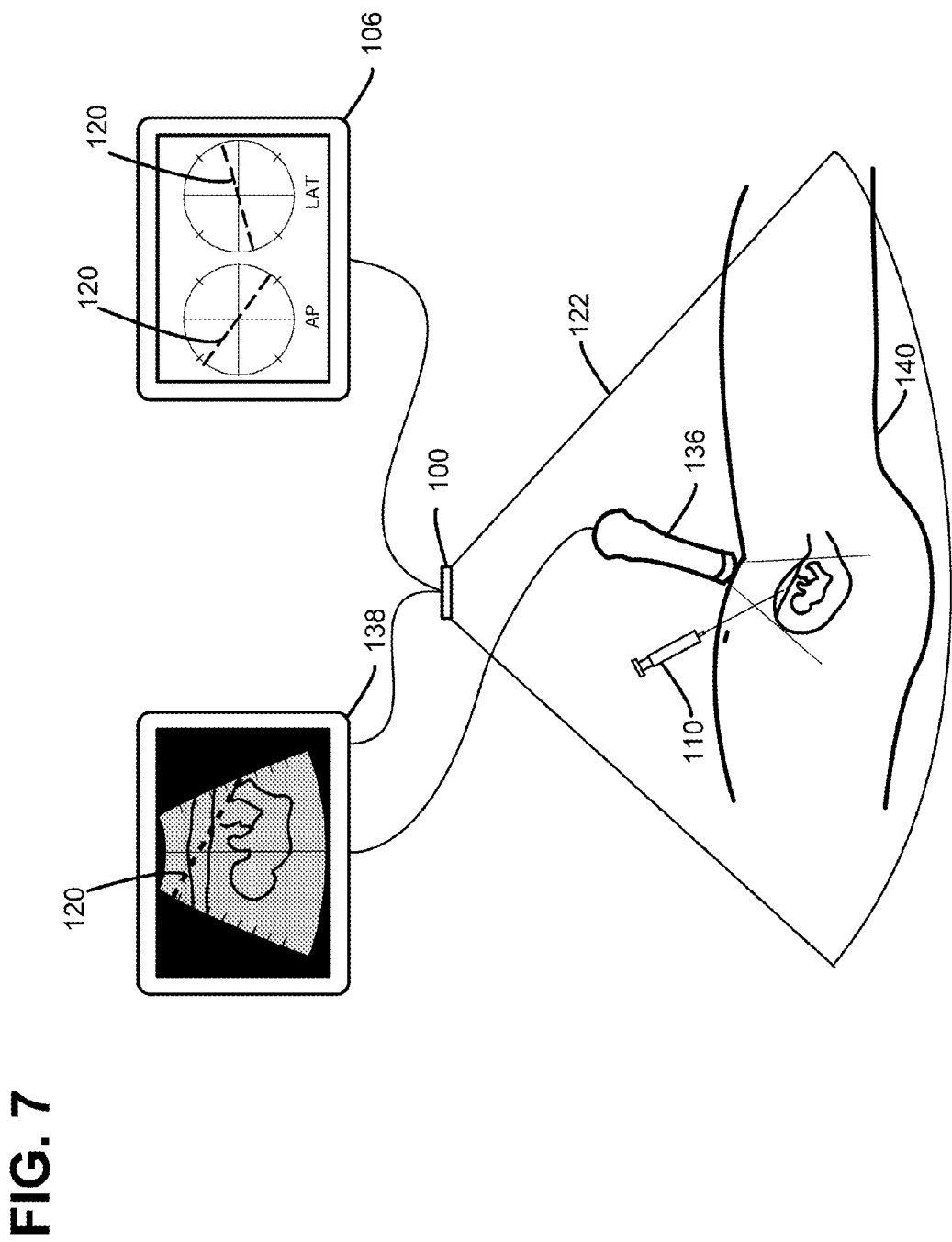
FIG. 7 illustrates a use case in ultrasound guided biopsy with the projection of a biopsy needle in an augmented display and the triangulation of the needle and the ultrasound on a primary display, in accordance with example embodiments.

Referring now to FIG. 7, in this embodiment, a patient's body 140 is shown with an ultrasound instrument 136 placed against it. Ultrasound instrument 136 is connected to an augmented ultrasound display 138. Sensor 100 is placed over the patient's body 140 so that sensor field 122 receives data from the working area, which includes the patient's body 140 and one or more instruments used in the working area, such as instrument 110. Sensor 100 is connected to both display 106 and augmented ultrasound display 138.

In this embodiment, the ultrasound instrument 136 is taking images of a female uterus while instrument 110 is being used obtain a biopsy deep within the patient's body 140. Projected instrument path 120 is shown overlaying the images from the ultrasound on the augmented ultrasound display 138 and on display 106.

Figure 8:
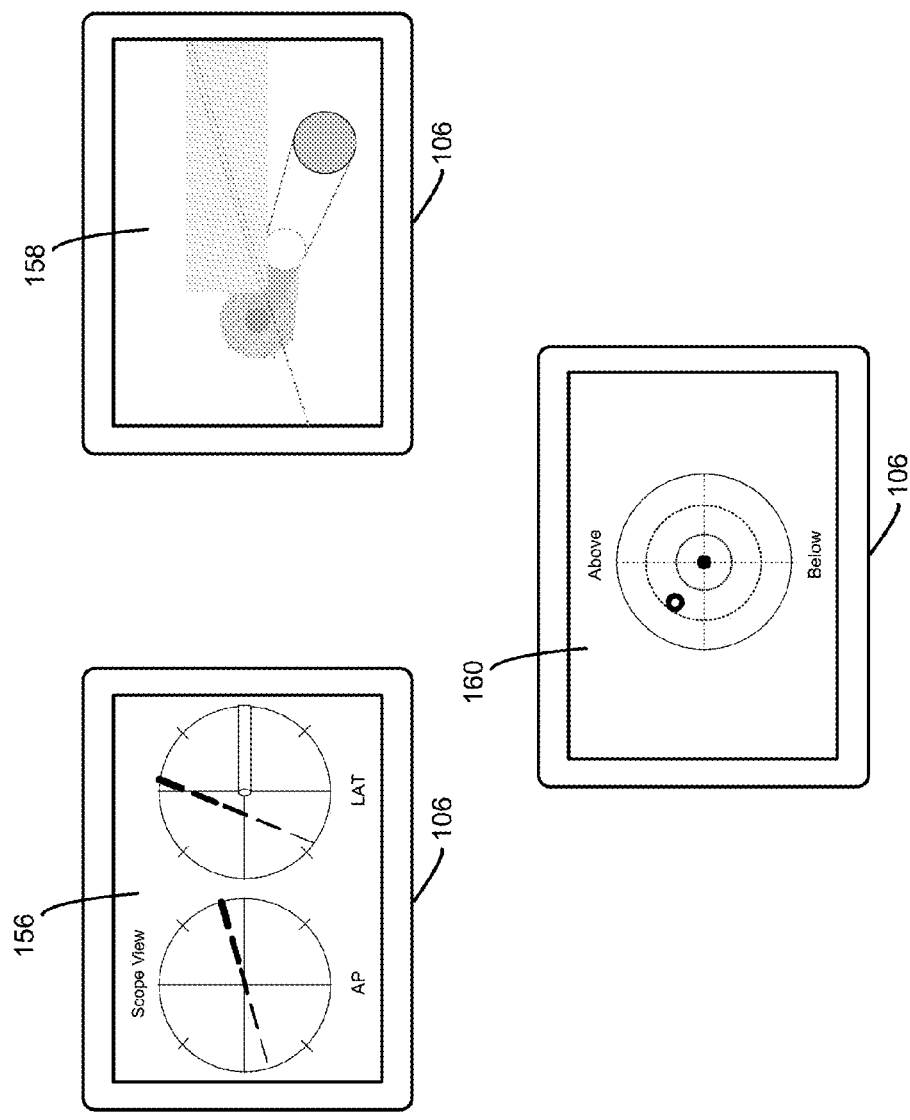
FIG. 8 depicts three types of displays that may be used to guide instruments: a display with orthogonal views, a three-dimensional rendered display, and a targeting display, in accordance with example embodiments.
Figure 9:
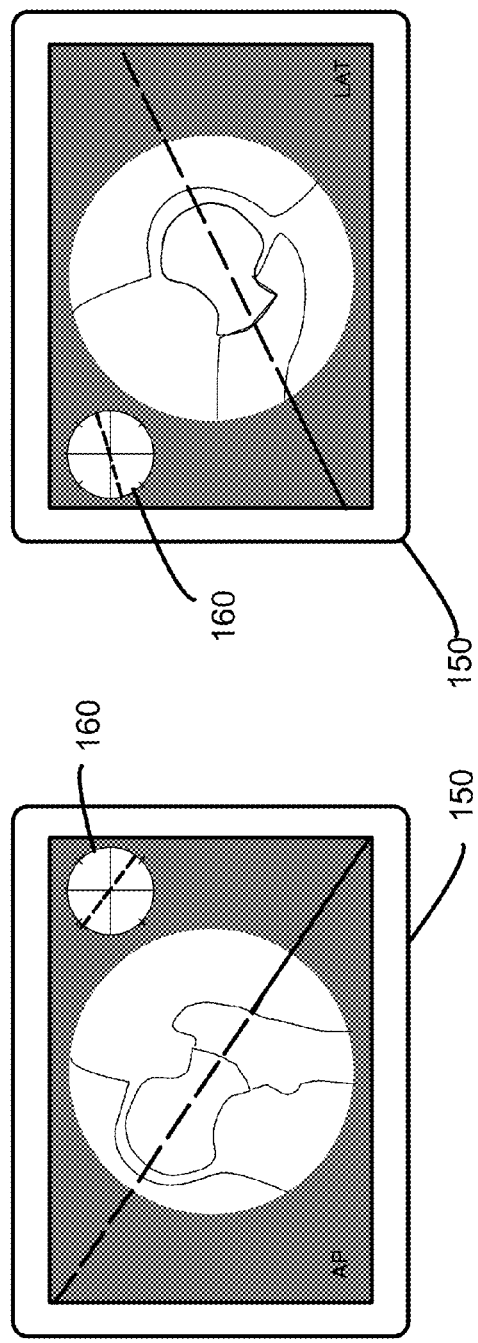
FIG. 9 depicts a primary display embedded within the augmented displays, in accordance with example embodiments.

Referring now to FIG. 8, the display 106 may show its data in various types of formats and views, including an orthogonal plane view 156, a three-dimensional rendered view 158, or a targeting view 160. Referring now to FIG. 9, display 106 may be shown as a virtual display 160 in augmented display 150, where augmented display 150 may be augmented arthroscopic display 134, augmented ultrasound display 138, augmented x-ray display 150, or some other type of augmented display. Display 106 may be shown as a virtual display 160 within the arthroscopic, ultrasound, x-ray, or other type of display without these displays being augmented.

Referring now to FIG. 10A, a procedure in which a target location is saved and then reacquired is depicted. At step (i), a greater tuberosity 164 of a shoulder 162 is the subject of an operation. Greater tuberosity 164 is shown on an augmented arthroscopic display 134. However, a virtual display may also be used in conjunction with or without the augmented display.

At step (ii), awl 166 is inserted into greater tuberosity 164 of shoulder 162, creating awl hole 174. A virtual representation 176 of awl 166 and its trajectory is shown in augmented display 134. At this point the virtual representation 176 of awl 166 and its trajectory is saved in the computer associated with augmented display 134 and/or the virtual display 160. The act of saving this information may be triggered by voice command, foot or hand pedals, motion of the user, or by direct input on the computer or display. An assistant may be used to trigger saving.

At step (iii), a tip of screw inserter 172 is placed against the skin of the patient. Based on the three-dimensional orientation of screw inserter 172, a virtual representation 178 of the trajectory of screw inserter 172 may appear on augmented display 134 and/or virtual display 160. Notably, virtual representation 178 is misaligned with target virtual representation 176 of awl 166. The computer associated with augmented display 134 and/or virtual display 160 may detect this misalignment, and alert the user of the misalignment. The alert may take the form of a visual or auditory cue.

At step (iv), screw inserter 172 is oriented such that its virtual representation 178 is aligned with virtual representation 176 of awl 166. The computer associated with augmented display 134 and/or virtual display 160 may detect this alignment, and alert the user of the alignment. The alert may take the form of a visual or auditory cue. Then, the user may insert screw inserter 172 into greater tuberosity 164 of shoulder 162.

Saving and recalling a target (e.g. the end of an instrument) has several other advantages. In one embodiment, the depth of a second instrument may be ascertained by referencing the saved target of a first instrument. For example, if an awl is placed into a greater tuberosity during arthroscopic shoulder surgery, the final endpoint of the awl could be saved as a target. If a second instrument, such as a screw, is placed into hole made by the awl, one could determine the depth of the screw placement relative to the awl by referencing the saved target. By referencing the saved target, the user may confirm that the screw is placed at the correct depth.

In a another embodiment, a second instrument could be advanced out of the trajectory of a first instrument, but aimed at the saved target of the first instrument (its tip). For example, a user may want to place the tip of an arthroscope at a point that he/she wants an arthroscopic drill to target from another portal. However, the user may not want to leave the arthroscope at this point. Thus, the user may save the position of the tip of the arthroscope as a target, and then withdraw the arthroscope to get a better field-of-view while advancing the tip of the drill to the saved target.

In yet another embodiment, two or more arthroscopic working portals may be created to converge on the same point (a saved target). For example, during arthroscopic Bankart repair, three portals may be created that enable a camera and two working instruments to be aligned to the same working area. The camera could be positioned in one portal. A spinal needle or another instrument may come in from a second portal, and the target (its tip) could be saved so that a third portal could be started that is in the trajectory of the target.

Figure 10B:
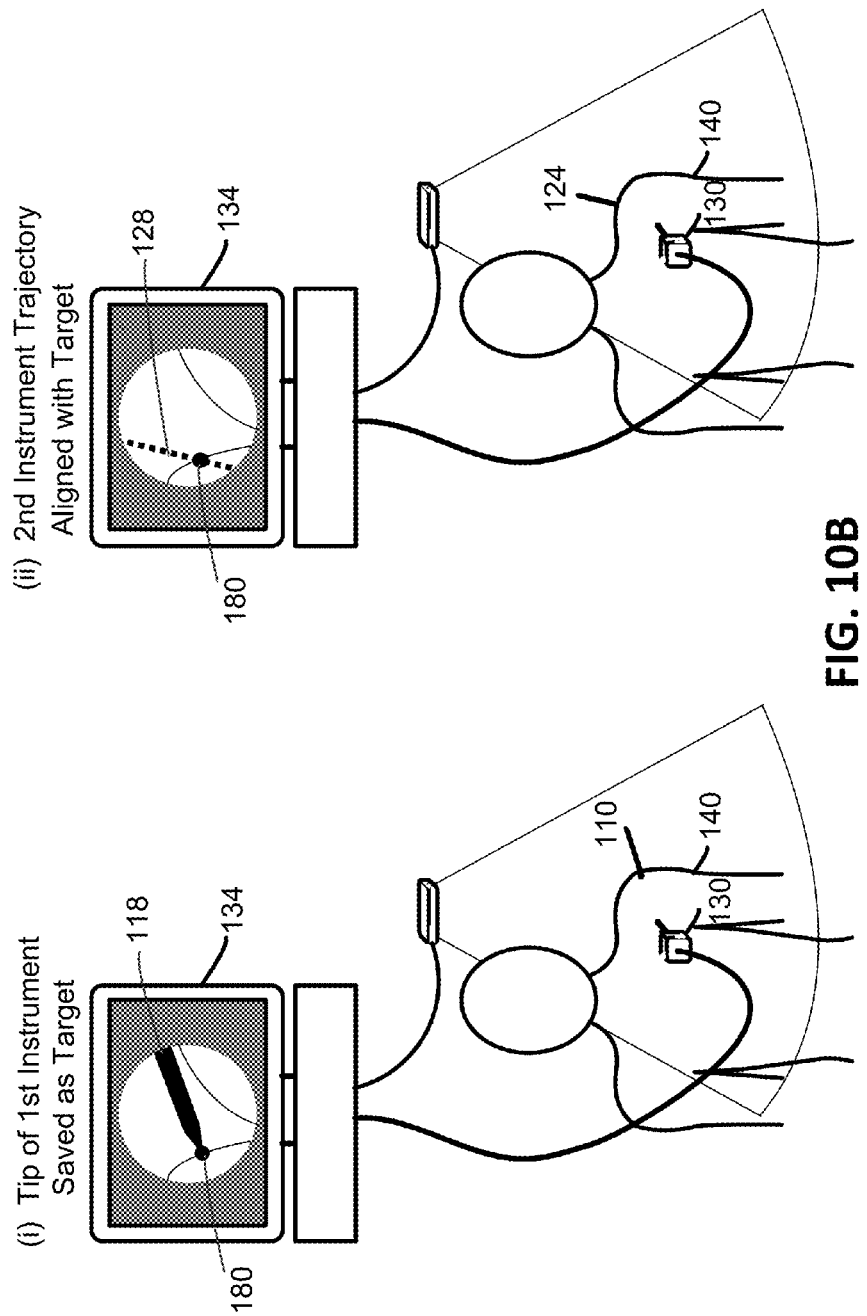
FIG. 10B depicts saving the position of a tip of an instrument during a procedure, then using the saved tip position to determine the alignment of another instrument used during the procedure, in accordance with example embodiments.

Referring to FIG. 10B, at step (i) an instrument 110 is positioned within the shoulder 162. Virtual representation 118 of instrument 110 is shown in the arthroscopic display 134. Virtual representation 180 of the tip of instrument 110 is saved as a target. The act of saving this information may be triggered by voice command, foot or hand pedals, motion of the user, or by direct input on the computer or display. An assistant may be used to trigger saving.

At step (ii), instrument 124 is placed at a different angle with respect to shoulder 162. Projected instrument path 128 of instrument 124 is shown in arthroscopic display 134. As can be seen in FIG. 10B, projected instrument path 128 crosses virtual representation 180, thereby aligning these two representations. The computer associated with augmented display 134 may detect this alignment, and alert the user of the alignment. The alert may take the form of a visual or auditory cue. The act of saving this information may be triggered by voice command, foot or hand pedals, motion of the user, or by direct input on the computer or display. An assistant may be used to trigger saving.

3. EXAMPLE COMPUTING DEVICE

Figure 11:
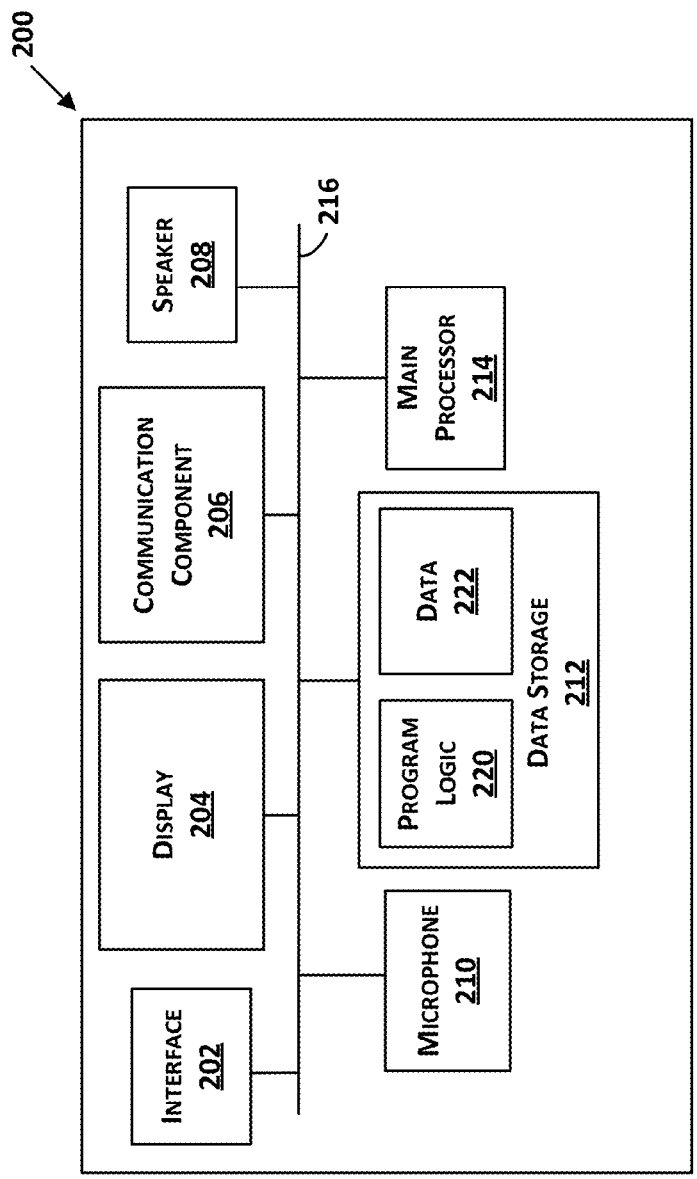
FIG. 11 depicts a controller, in the form of a computing device, in accordance with example embodiments.

FIG. 11 illustrates a schematic drawing of an example computing device 200. Thus, computing device 200 may take the form of any computing device, such as a controller, a client device, a server device, a wireless computing device, a tablet device, and so on. In some examples, components illustrated in FIG. 2 may be distributed across multiple computing devices. Nonetheless, computing device 200 could take other forms than a general purpose computer. For instance, computing device 200 may incorporate field-programmable gate arrays, application specific integrated circuits, and/or other forms of digital logic.

Computing device 200 may interoperate with sensor 100 and display 106 to carry out and/or facilitate any of the embodiments herein. In some cases, computing device 200 may be integrated with display 106 (e.g., display 106 may be part of computing device 200). In other cases, computer 200 may take the form of a controller integrated with display 106.

In some implementations, computing device 200 may include a device platform or operating system (not shown). The device platform may include different applications and an application framework, as well as various kernels, schedulers, memory managers, libraries, and runtime entities. In some examples, other formats or systems may operate on controller 200 as well.

Computing device 200 may include an interface 202, a display 204, a communication component 206, a speaker 208, a microphone 210, data storage 212, and a main processor 214. Components illustrated in FIG. 2 may be linked together by a communication bus 216. Computing device 200 may also include additional hardware to enable further functionality and/or operations.

Interface 202 may be configured to allow a user to interact with computing device 200. Thus, interface 202 may include user-interface components, such as a keyboard, touchscreen, touchpad, presence-sensitive input device, display, etc.

Display 204 may include a screen for emitting output images. Thus, display 204 may be a monitor, television screen, touchscreen, and so on. In some embodiments of computing device 200, such as a tablet computer, display 204 may integrated with interface 202. In some embodiments, display 204 may be the same component as display 106.

Communication component 206 may be a communication interface that is configured to facilitate wireless and/or wireline data and/or voice communication according to standard or non-standard communication protocols. For example, communication component 206 may be configured to enable a communication interface that is configured to facilitate wireless data communication according to one or more wireless communication standards or non-standard protocols. For example, communication component 206 may include a Wifi interface that is configured to facilitate wireless data communication according to one of the 802.11 protocols. As another example, communication component 206 may include a Bluetooth interface that is configured to facilitate wireless data communication according to one or more Bluetooth protocols. Alternatively or additionally, communication component 206 may facilitate wide-area wireless data communication according to Code Division Multiple Access (CDMA), Worldwide Interoperability for Microwave Access (WIMAX), Universal Mobile Telecommunications System (UMTS), Long Term Evolution (LTE). In some embodiments, communication component 206 may include an Ethernet interface, or another type or wireline interface.

Speaker 208 may be any type of apparatus that can produce sound. In some cases, speaker 208 may convert digital representations of sounds (e.g., digitally encoded voice or music signals) into audible analog representations of the sounds. Speaker 208 may be integrated with computing device 200, or may exist as a removable module (e.g., headphones or an external speaker).

Microphone 210 may be any type of apparatus that can receive analog sound. In some cases, microphone 210 may convert analog representations of sounds into digital representations of these sounds. Like speaker 208, microphone 210 may exist as a removable module (e.g., an external microphone).

Data storage 212 may store program logic 220 that can be accessed and executed by main processor 214. Program logic 220 may include machine-readable instructions that, when executed by main processor 214, cause computing device 200 to carry out various operations and procedures. Data storage 212 may also store data 222 that may include data collected by any of interface 202, communication component 206, and/or microphone 210. Data storage 212 may store additional data as well. Data storage 212 may be a non-transitory computer-readable data medium, such as a hardware memory module.

Main processor 214 may be any type of one or more microprocessors or general-purpose processors. However, main processor 214 may be integrated with or include various types of co-processors, network processors, graphics processors, and/or digital logic.

Communication bus 216 is illustrated as a wired connection; however, wireless connections may also be used. For example, communication bus 216 may be a wired serial bus, such as a universal serial bus (USB), or a parallel bus. Alternatively or additionally, communication bus 216 may be a wireless connection using, e.g., short-range wireless radio technology, communication protocols described in IEEE 802.11 (including any IEEE 802.11 revisions), or cellular technology, among other possibilities.

4. EXAMPLE OPERATIONS

Figure 12:
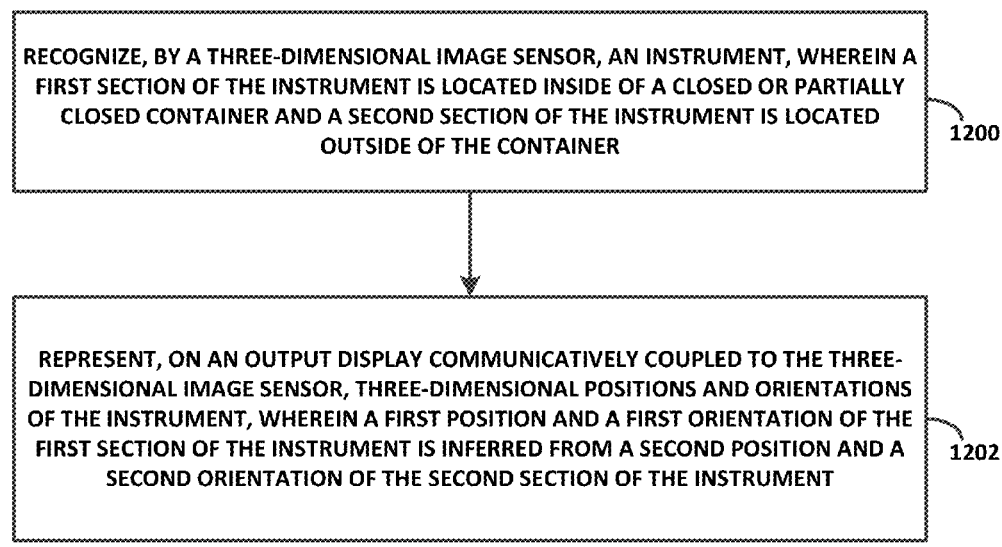
FIG. 12 is a flow chart, in accordance with example embodiments.

FIG. 12 is a flow chart illustrating an example embodiment. The embodiment illustrated by this figure may be carried out by a computer, such as computing device 200. However, the embodiment can be carried out by other types of devices or device subsystems, such as a controller, digital logic, or other computing systems. Further, various steps of the flow chart may be carried out by one or more of sensor 100 or display 106, either or both of which may be integrated with computing device 200. Additionally, the embodiments herein may be combined, and may incorporate any aspect or feature disclosed in this specification or the accompanying drawings.

A possible arrangement may include a three-dimensional image sensor configured to scan an area including a closed or partially closed container, an output display, and a controller. In accordance with step 1200 of FIG. 12, the controller may be configured to recognize an instrument that is detected by the three-dimensional image sensor, where a first section of the instrument is located inside of the container and a second section of the instrument is located outside of the container. In some embodiments, the container may be a body of an organism, and the instrument may be a surgical instrument located partially within the body. Other types of containers and instruments are possible.

In accordance with step 1202 of FIG. 12, the controller may also be configured to represent, on the output display, three-dimensional positions and orientations of the instrument, where a first position and a first orientation of the first section of the instrument is inferred from a second position and a second orientation of the second section of the instrument. In some embodiments, the instrument is not equipped with specialized attachments that help track the orientation and motion of the instrument.

The displayed three-dimensional positions and orientations may be rendered in a three-dimensional representation on the output display, or may be rendered using two or more two-dimensional representations (e.g., an X/Y plane representation and a Y/Z plane representation, an X/Z plane representation and a Y/Z plane representation, or an X/Y plane representation and an X/Z plane representation).

In some embodiments, the three-dimensional image sensor uses at least one camera and at least one light-emitting diode to scan the container. The controller may be further configured to determine a three-dimensional representation of the container and contents of the container from the scan. Multiple cameras and/or multiple light-emitting diodes may be used. In some cases, the cameras may capture images outside of the human-visible light spectrum (e.g., infrared or ultraviolet). Alternatively or additionally, sources of light other than light-emitting diodes may be used.

In some embodiments, the controller may be further configured to represent, on the output display, a virtual trajectory of the instrument. This virtual trajectory may extend from the first section of the instrument away from the instrument along a longitudinal axis of the instrument. The controller may also be configured to save the virtual trajectory of the instrument, and possibly represent, on the output display, the saved virtual trajectory by itself or along with a second virtual trajectory of a second instrument. The controller may be further configured to determine whether the saved virtual trajectory is aligned or misaligned with the second virtual trajectory, and to provide an alert indicating the alignment or misalignment.

In some embodiments, the two virtual trajectories may be considered aligned if both represent the same or substantially identical vectors in three-dimensional space. Herein, substantially identical vectors deviate from one another by no more than a threshold angle (e.g., 1 degree, 2 degrees, 5 degrees, etc.) in any of the three dimensions. In other embodiments, the two virtual trajectories may be considered aligned if they meet at some point within the container.

In some embodiments, an end of the instrument may be placed against an outer side of the container, and the controller may be configured to display, on the output display, a projected virtual trajectory of the instrument. This virtual trajectory may extend from the end of the instrument into the container along the longitudinal axis of the instrument, or along any other directional axis on which the instrument is moving. Similar to the embodiments above, this virtual trajectory and/or the instrument endpoint may be saved and recalled as well. In this way, the recalled virtual trajectory may be used for targeting of an instrument.

In some embodiments, the controller is further configured to, prior to recognizing the instrument, (i) register the instrument, as well as a size and a shape of the instrument, and (ii) save a representation of the size and the shape of the instrument. The controller may be further configured to, during recognition of the instrument, automatically identify the instrument based on the saved representation. Thus, a user can pre-register one or more instruments prior to utilizing those instruments in conjunction with the container, and the controller may automatically identify the instruments, as well as their physical characteristics (e.g., size, shape, etc.). In some cases, the controller may be associated with a database that stores information regarding the physical characteristics of various instruments, and the controller may identify an instrument in use by comparing a representation of this instrument with the information in the database.

In some embodiments, the output display may be that of medical imaging equipment, and wherein representing the three-dimensional positions and orientations of the instrument comprises overlaying the three-dimensional positions and orientations of the instrument on output from the medical imaging equipment. For example, the medical imaging equipment may be arthroscopic imaging equipment, ultrasound imaging equipment, or x-ray imaging equipment.

In some embodiments, the instrument has a total longitudinal length and a longitudinal axis that spans the first section and the second section. Inferring the first position and the first orientation of the first section from the second position and the second orientation of the second section may involve projecting the longitudinal axis from the second section into the container for a distance such that a first longitudinal length of the first section plus an inferred second longitudinal length of the second section is substantially equal to the total longitudinal length. For purposes of this inference, substantial equality is satisfied when the first longitudinal length of the first section plus the second longitudinal length is within a threshold of the total longitudinal length (e.g., 1 millimeter, 2 millimeters, 5 millimeters, 10, millimeters, etc.).

5. CONCLUSION

The present disclosure is not to be limited in terms of the particular embodiments described in this application, which are intended as illustrations of various aspects. Many modifications and variations can be made without departing from its scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of the disclosed systems, devices, and methods with reference to the accompanying figures. The example embodiments described herein and in the figures are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the message flow diagrams, scenarios, and flow charts in the figures and as discussed herein, each step, block, and/or communication can represent a processing of information and/or a transmission of information in accordance with example embodiments. Alternative embodiments are included within the scope of these example embodiments. In these alternative embodiments, for example, functions described as steps, blocks, transmissions, communications, requests, responses, and/or messages can be executed out of order from that shown or discussed, including substantially concurrent or in reverse order, depending on the functionality involved. Further, more or fewer blocks and/or functions can be used with any of the ladder diagrams, scenarios, and flow charts discussed herein, and these ladder diagrams, scenarios, and flow charts can be combined with one another, in part or in whole.

A step or block that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical functions or actions in the method or technique. The program code and/or related data can be stored on any type of computer readable medium such as a storage device including a disk, hard drive, or other storage medium.

The computer readable medium can also include non-transitory computer readable media such as computer-readable media that store data for short periods of time like register memory, processor cache, and random access memory (RAM). The computer readable media can also include non-transitory computer readable media that store program code and/or data for longer periods of time. Thus, the computer readable media may include secondary or persistent long term storage, like read only memory (ROM), optical or magnetic disks, compact-disc read only memory (CD-ROM), for example. The computer readable media can also be any other volatile or non-volatile storage systems. A computer readable medium can be considered a computer readable storage medium, for example, or a tangible storage device.

Moreover, a step or block that represents one or more information transmissions can correspond to information transmissions between software and/or hardware modules in the same physical device. However, other information transmissions can be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

Additionally, any enumeration of elements, blocks, or steps in this specification or the claims is for purposes of clarity. Thus, such enumeration should not be interpreted to require or imply that these elements, blocks, or steps adhere to a particular arrangement or are carried out in a particular order.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A device comprising:
a three-dimensional, depth-sensing optical image sensor;
a memory;
an output display; and
a controller configured to:
receive, from the three-dimensional, depth-sensing optical image sensor, data regarding a second section of an instrument that was optically detected by the three-dimensional, depth-sensing optical image sensor, wherein a first section of the instrument is located inside of a closed or partially-closed container and the second section of the instrument is located outside of the container, and wherein the first section of the instrument is not visible from outside of the container,
determine, using the data, a three-dimensional position and a three-dimensional orientation of the second section of the instrument,
infer a three-dimensional position and a three-dimensional orientation of the first section of the instrument from the three-dimensional position and the three-dimensional orientation of the second section of the instrument,
represent, on the output display, the inferred three-dimensional position and the inferred three-dimensional orientation of the first section of the instrument,
represent, on the output display, a virtual trajectory of the instrument extending from the first section of the instrument away from the instrument and into the container along a longitudinal axis of the instrument,
save, in the memory, the virtual trajectory of the instrument,
represent, on the output display, the saved virtual trajectory of the instrument along with a second virtual trajectory of a second instrument, and
provide an alert indicating whether a longitudinal axis of the saved virtual trajectory is aligned or misaligned with a longitudinal axis of the second virtual trajectory.

2. The device of claim 1, wherein the three-dimensional, depth-sensing optical image sensor includes at least one camera and at least one light-emitting diode.

3. The device of claim 1, wherein the controller is further configured to, prior to determining the three-dimensional position and the three-dimensional orientation of the second section of the instrument, (i) register the instrument, as well as a size and a shape of the instrument, and (ii) save a representation of the size and the shape of the instrument.

4. The device of claim 3, wherein the controller is further configured to automatically identify the instrument based on the saved representation.

5. The device of claim 1, wherein the output display is that of medical imaging equipment, and wherein representing the three-dimensional position and orientation of the instrument comprises overlaying the three-dimensional position and orientation of the instrument on output from the medical imaging equipment.

6. The device of claim 5, wherein the medical imaging equipment is selected from the group consisting of arthroscopic imaging equipment, ultrasound imaging equipment, and x-ray imaging equipment.

7. The device of claim 1, wherein the instrument has a total longitudinal length, and wherein inferring the three-dimensional position and the three-dimensional orientation of the first section of the instrument from the three-dimensional position and the three-dimensional orientation of the second section of the instrument comprises:
  determining, from the second section of the instrument, the longitudinal axis of the instrument;
  determining a longitudinal length of the second section of the instrument, and
  projecting the longitudinal axis of the instrument into the container for a distance such that a longitudinal length of the first section of the instrument plus the determined longitudinal length of the second section of the instrument is substantially equal to the total longitudinal length.

8. A method comprising:
  receiving, from a three-dimensional, depth-sensing image sensor, data regarding a second section of an instrument that was optically detected by the three-dimensional, depth-sensing image sensor, wherein a first section of the instrument is located inside of a closed or partially-closed container and the second section of the instrument is located outside of the container, and wherein the first section of the instrument is not visible from outside of the container;
  determining, using the data, a three-dimensional position and a three-dimensional orientation of the second section of the instrument;
  inferring a three-dimensional position and a three-dimensional orientation of the first section of the instrument from the three-dimensional position and the three-dimensional orientation of the second section of the instrument;
  representing, on an output display communicatively coupled to the three-dimensional, depth-sensing image sensor, the inferred three-dimensional position and the inferred three-dimensional orientation of the first section of the instrument;
  representing, on the output display, a virtual trajectory of the instrument extending from the first section of the instrument away from the instrument and into the container along a longitudinal axis of the instrument;
  saving, in a memory, the virtual trajectory of the instrument;
  representing, on the output display, the saved virtual trajectory of the instrument along with a second virtual trajectory of a second instrument; and
  providing an alert indicating whether a longitudinal axis of the saved virtual trajectory is aligned or misaligned with a longitudinal axis of the second virtual trajectory.

9. The method of claim 8, wherein the three-dimensional, depth-sensing image sensor includes at least one camera and at least one light-emitting diode.

10. The method of claim 8, further comprising:
  prior to determining the three-dimensional position and the three-dimensional orientation of the second section of the instrument, (i) registering the instrument, as well as a size and a shape of the instrument, and (ii) saving a representation of the size and the shape of the instrument.

11. The method of claim 8, wherein the output display is that of medical imaging equipment, and wherein representing the three-dimensional position and orientation of the instrument comprises overlaying the three-dimensional position and orientation of the instrument on output from the medical imaging equipment.

12. The method of claim 8, wherein the instrument has a total longitudinal length, and wherein inferring the three-dimensional position and the three-dimensional orientation of the first section of the instrument from the three-dimensional position and the three-dimensional orientation of the second section of the instrument comprises:
  determining, from the second section of the instrument, the longitudinal axis of the instrument;
  determining a longitudinal length of the second section of the instrument; and
  projecting the longitudinal axis of the instrument into the container for a distance such that a first longitudinal length of the first section of the instrument plus the determined longitudinal length of the second section of the instrument is substantially equal to the total longitudinal length.

13. A system comprising:
  a three-dimensional, depth-sensing optical image sensor;
  an output display; and
  a computing device communicatively coupled to the three-dimensional, depth-sensing optical image sensor and the output display, wherein the computing device includes a processor and a memory, and wherein instructions stored in the memory are executable by the processor to perform operations including:
    receiving, from the three-dimensional, depth-sensing optical image sensor, data regarding a second section of an instrument that was optically detected by the three-dimensional, depth-sensing optical image sensor, wherein a first section of the instrument is located inside of a closed or partially-closed container and the second section of the instrument is located outside of the container, and wherein the first section of the instrument is not visible from outside of the container,
    determining, using the data, a three-dimensional position and a three-dimensional orientation of the second section of the instrument,
    inferring a three-dimensional position and a three-dimensional orientation of the first section of the instrument from a three-dimensional position and a three-dimensional orientation of the second section of the instrument,
    representing, on the output display, the inferred three-dimensional position and the inferred three-dimensional orientation of the first section of the instrument,
    representing, on the output display, a virtual trajectory of the instrument extending from the first section of the instrument away from the instrument and into the container along a longitudinal axis of the instrument,
    saving, in the memory, the virtual trajectory of the instrument,
    representing, on the output display, the saved virtual trajectory of the instrument along with a second virtual trajectory of a second instrument, and
    providing an alert indicating whether a longitudinal axis of the saved virtual trajectory is aligned or misaligned with a longitudinal axis of the second virtual trajectory.

* * * * *